United States Patent [19]

Turk et al.

[11] B 3,996,239

[45] Dec. 7, 1976

[54] CONVERSION OF ALIPHATIC NITRILES TO CARBOXYLIC ACIDS USING CYCLIC ACID ANHYDRIDES

[75] Inventors: Stanley D. Turk; Charles A. Drake, both of Bartlesville, Okla.

[73] Assignee: Phillips Petroleum Company, Bartlesville, Okla.

[22] Filed: Sept. 17, 1973

[21] Appl. No.: 398,084

[44] Published under the second Trial Voluntary Protest Program on February 3, 1976 as document No. B 398,084.

[52] U.S. Cl. .................. 260/326 R; 260/326.5 B; 260/537 N
[51] Int. Cl.² ............ C07D 209/48; C07D 209/52
[58] Field of Search ..... 260/326 R, 537 N, 326.5 B

[56] References Cited

UNITED STATES PATENTS 3,720,679    3/1973    Feldman et al. .................. 260/281

OTHER PUBLICATIONS

Komori et al., Chem. Abs. 49, 6836a (1953).
M. T. Dangyan et al., Chem. Abs. 40, 3399–3401 (1946).

*Primary Examiner*—Paul M. Coughlan, Jr.
*Assistant Examiner*—Mark L. Berch

[57] ABSTRACT

Simultaneous production of an aliphatic carboxylic acid and a carboxylic acid imide is achieved through the reaction of an aliphatic nitrile and an acid anhydride in the presence of water and a strong acid.

4 Claims, No Drawings

CONVERSION OF ALIPHATIC NITRILES TO CARBOXYLIC ACIDS USING CYCLIC ACID ANHYDRIDES

This invention relates to the simultaneous production of aliphatic carboxylic acids and carboxylic acid imides.

The acid or base hydrolysis of a nitrile to the corresponding carboxylic acid is well known. Nitriles are, however, difficult to hydrolyze. Prolonged heating under reflux with a strong acid or base is required to effect cleavage. Even moderately hindered compounds are often inert toward hydrolysis for all practical purposes. Further, large amounts of acid or base are generally required to promote hydrolysis. Relatively large amounts of base or acid are required to neutralize the hydrolysis promoter.

Similarly, processes for the preparation of carboxylic acid imides are well known. Such processes generally involve the reaction of carboxylic acid anhydrides with ammonia or amines. Such processes generally require separation of the intermediate amide prior to conversion of the amide to the imide.

Each of the above processes suffer one or more serious drawbacks. The more prominent drawbacks are large volumes of hydrolysis promoter and neutralizer, prolonged heating, and separation of intermediates.

Accordingly, it is an object of this invention to provide an improved process for producing aliphatic carboxylic acids.

It is another object to provide an improved process for producing carboxylic acid imides.

It is a further object to provide a process for the simultaneous production of a carboxylic acid and a carboxylic acid imide.

Other aspects, objects, and advantages will become apparent to those skilled in the art upon consideration of the following disclosure.

In accordance with this invention there is provided a process for the production of an aliphatic carboxylic acid from the corresponding nitrile which does not require prolonged heating at reflux with a strong acid or base. Neither does it require neutralization of the hydrolysis promoter.

There is also provided a process for the production of a carboxylic acid imide which does not require separation of the intermediate amide. There is further provided a process for the simultaneous production of an aliphatic carboxylic acid and a carboxylic acid imide which comprises reacting an aliphatic nitrile with a carboxylic acid anhydride in the presence of water and a strong acid.

The process of this invention can be represented by the following general reaction

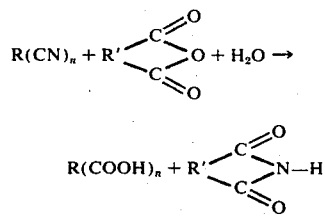

wherein R is an alkyl or alkylene group having from 1 to 15 carbon atoms, or a cycloalkyl or cycloalkylene group having up to 13 carbon atoms and having from 0 to 1 ethylenic double bonds, $n$ is an integer having a value of 1 or 2, and R' is a cycloalkylene, arylene or alkarylene radical having from 6 to 12 carbon atoms.

More particularly, in the above formulae, when n is 1, R is selected from the group consisting of alkyl, cycloalkyl and alkenyl, which alkenyl group possesses one double bond; and when $n$ is 2, R is selected from the group consisting of alkylene, cycloalkylene and alkenylene, which alkenylene possesses one double bond, wherein the R group contains up to 13 carbon atoms. R' can be an arylene group having 6 or 10 carbon atoms, an alkarylene group having from 7 to 12 carbon atoms or a cycloalkylene group having from 6 to 12 carbon atoms. Preferably, the carbon atoms of the anhydride group are bonded to adjacent carbon atoms of the ring structure.

Examples of nitrile compounds that can be used in the process of this invention are acetonitrile, butyronitrile, n-dodecylnitrile, cyclohexylnitrile, pimelonitrile, suberonitrile, 5-methylene azelaonitrile, azelaonitrile, adiponitrile and the like.

Preferably, the acid anhydrides for use in the process of this invention are the anhydrides of aromatic and cycloaliphatic carboxylic acids having two carboxyl groups bonded to adjacent carbon atoms of the ring structure, as for example, phthalic anhydride, 4-n-butyl phthalic anhydride, 4,5-di-n-propyl phthalic anhydride, hexahydrophthalic anhydride, tetrahydrophthalic anhydride and the like.

The nitrile and anhydride are generally employed in stoichiometric amounts; that is, there are usually present one anhydride group for each nitrile group. If desired, however, a slight excess of either material can be employed.

Water is generally used in the process in amounts ranging from stoichiometric to a slight excess. There is usually present one stoichiometric unit of water for each anhydride/nitrile stoichiometric unit.

Catalytic amounts of strong acids are required in the process of this invention. In general, acids which exhibit a relatively high degree of ionization in water solution can be used. Examples of suitable inorganic acids are hydrochloric acid, sulfuric acid, phosphoric acid and the like; examples of suitable organic acids are trichloroacetic acid, p-toluenesulfonic acid and the like. Also useful are Lewis acids such as hydrogen fluoride, boron trifluoride, aluminum chloride, zinc chloride and the like. Such acids are used in amounts ranging from about 0.01 to about 3 weight percent based upon the total weight of reactants. In a presently preferred embodiment, phosphoric acid is used in an amount ranging from about 0.25 to about 1 weight percent.

Reaction times and temperatures are dependent on starting materials and the desired conversion or product distribution. In general, times of from 0.5 to about 20 hours at temperatures of from 100° to about 350° C are sufficient to produce the desired results.

The process is conducted in a pressure vessel, such as an autoclave, wherein reaction pressures can be autogenous. That is, the reaction pressure can be self-generated, dependent upon the size of the reaction vessel and the quantity and nature of the reactants. If desired, the pressure can be increased by an external source to from 0 to about 5000 psig.

In a preferred embodiment, the reactor vessel is purged with an inert gas before conducting the process of this invention.

The reaction can be carried out in the presence or absence of diluents. Diluents such as aromatic or saturated cyclic or acyclic paraffinic hydrocarbons, tert-amines, ethers, thioethers, sulfoxides, sulfones and the like can be employed. In a preferred embodiment, the diluent is benzene.

Separation and recovery of reaction end products can be accomplished by means generally employed in the art. For example, the following methods can be used: filtration, distillation, crystallization, solvent extraction, and the like. Selection of the method of separation and recovery will be evident to those skilled in the art.

The following example further illustrates the invention.

EXAMPLE 225 g (1.52 moles) of phthalic anhydride, 121.5 g (0.75 mole) of 5-methylene-1,9-nonanedinitrile, 300 cc of benzene, 40 g of water and 2 g of phosphoric acid were placed in a 1-liter autoclave. The autoclave was closed, then purged with dry nitrogen. Following purging, the reactor was heated to 240° C for a period of 4 hours. After cooling, the reaction mixture was filtered. The filter solid, after being washed in 300 cc of benzene, filtered and dried, yielded 220 g of phthalimide having a melting point of 234°–238° C. Yield 100 percent.

The two filtrates were combined and the benzene was removed by evaporation. The liquid residue was distilled through a short path distillation apparatus at reduced pressure. There was recovered 128 g of 5-methylene-1,9-nonanedioic acid, having a boiling range of 195°–212° C, at 0.5 mm Hg. Yield 85.5 percent.

This example illustrates that simultaneous complete conversion of starting material with high product selectivity and high product yields of acid and imide is achieved in accordance with the process of this invention.

The mono- and di-carboxylic acids of the present invention can be used to produce well-known products, such as polyesters, polyamides, and the like, for polymer applications and esters for use as plasticizers.

Reasonable variations and modifications can be made without departing from the spirit and scope of this disclosure and the appended claims.

We claim:

1. A process for the simultaneous preparation of an aliphatic carboxylic acid and an imide from the corresponding aliphatic nitrile and carboxylic acid anhydride, respectively, which comprises the step of reacting said nitrile with said anhydride and water in the presence of a catalytic amount of a strong acid wherein said nitrile has the formula

wherein $n$ is an integer having a value of 1 or 2, wherein for $n = 1$, R is selected from the group consisting of alkyl, cycloalkyl and alkenyl (said alkenyl possessing one double bond), and for $n = 2$, R is selected from the group consisting of alkylene, cycloalkylene and alkenylene (said alkenylene possessing one double bond) with the proviso that said R group contains up to 13 carbon atoms; and wherein said anhydride has the formula

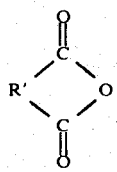

wherein R' is selected from the group consisting of arylene groups having 6 or 10 carbon atoms, alkarylene groups having from 7 to 12 carbon atoms and cycloalkylene groups having from 6 to 12 carbon atoms, wherein the carbon atoms of the anhydride group are bonded to adjacent carbon atoms of the ring structure; wherein said reaction is conducted at a pressure in the range of autogenous pressure to 5000 pounds above autogenous pressure, at a temperature ranging from about 100° to about 350°C for a time ranging from about 0.5 to about 20 hours.

2. The process of claim 1 wherein said strong acid is present in an amount ranging from about 0.01 to about 3 weight percent based upon the combined weight of said nitrile and said anhydride.

3. The process of claim 2 wherein said nitrile is reacted in stoichiometric quantities with said anhydride.

4. The process of claim 3 wherein said nitrile is 5-methylene-1,9-nonanedinitrile, said anhydride is phthalic anhydride and said strong acid is phosphoric acid.

* * * * *